United States Patent [19]

Kraus et al.

[11] Patent Number: 5,401,869
[45] Date of Patent: Mar. 28, 1995

[54] PROCESS FOR THE PREPARATION OF AMINOMETHYLENE COMPOUNDS

[75] Inventors: Helmut Kraus, Cologne; Nikolaus Müller, Monheim; Gerhard Marzolph, Cologne; Bernhard Beitzke, Rösrath, all of Germany

[73] Assignee: Bayer Aktiengesellschaft, Leverkusen, Germany

[21] Appl. No.: 184,314

[22] Filed: Jan. 21, 1994

[30] Foreign Application Priority Data

Jan. 27, 1993 [DE] Germany .......................... 43 02 156.5

[51] Int. Cl.⁶ .................. C07C 253/30; C07C 211/21; C07C 67/00
[52] U.S. Cl. ...................... 558/375; 544/161; 544/162; 544/163; 544/171; 546/192; 546/230; 546/238; 548/566; 548/571; 548/572; 558/384; 560/9; 560/22; 560/23; 560/38; 560/41; 560/43; 560/147; 560/156; 560/170; 560/171
[58] Field of Search ...................... 558/375; 560/9, 22, 560/23, 38, 41, 43, 147, 171

[56] References Cited

U.S. PATENT DOCUMENTS 5,095,133  3/1992  Blank et al. ........................ 558/375

OTHER PUBLICATIONS

J. Org. Chem. 46 (1981), 1752.
Org. Synth. 63 (1985), 214.
Chem. Ber. 97 (1964), 3397.

*Primary Examiner*—Paul J. Killos
*Attorney, Agent, or Firm*—Sprung Horn Kramer & Woods

[57] ABSTRACT

Aminomethylene compounds of the formula

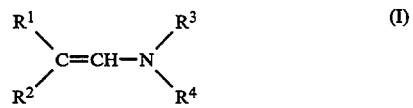

(I)

may advantageously be prepared by reacting C—H-acidic compounds of the formula

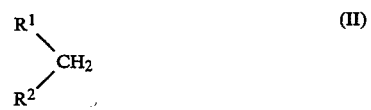

(II)

with formamide acetals of the formula

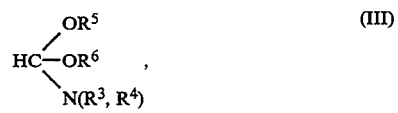

(III)

in which the radicals $R^1$ to $R^6$ have the meaning given in the description, if the process is carried out in the presence of a secondary amine of the formula

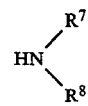

in which $R^7$ and $R^8$ have the meaning given in the description.

7 Claims, No Drawings

PROCESS FOR THE PREPARATION OF AMINOMETHYLENE COMPOUNDS

The invention relates to a process for preparing aminomethylene compounds (enamines) by reacting C—H acidic compounds with formamide acetals using a catalytic quantity of a secondary amine.

Enamines, such as, for example, aminomethylenated malonic acid esters, acetic acid esters, nitriles, 2-nitrotoluenes or picolines, are important structural components for preparing heterocycles, such as pyrazoles, pyrimidines, quinolines or indoles, which are used as pharmaceutical active compounds or plant-protection agents.

In the past, a large number of processes have been described for aminomethylenating; some of the important ones are mentioned and discussed in DE-A 39 25 720.

The use of ortho amides leads to technically simple processes, since, in addition to the desired reaction product, only readily volatile components arise. Depending on the C—H acidity of the starting material, the industrially available DMF acetal may be sufficient, or else it may be necessary to use aminal esters or even tris-aminomethanes.

J. Org. Chem. 46 (1981), 1752 describes how the reactivity of the DMF acetal can be drastically increased if at least one equivalent of a cyclic secondary amine is added during the reaction. For example, the use of pyrrolidine as the reactive amine lowers the reaction time for an aminomethylenation from 51 to 3 hours (Org. Synth. 63 ( 1985 ), 214 ).

The increased reactivity is explained on the basis of the intermediate formation of pyrrolidino aminal esters or pyrrolidino tris-amino compounds. However, such species dimerize at relatively low temperatures to give tetra-aminoethenes, which can lead to drastic reductions in yield. Thus, a temperature of 100° C. is sufficient to cause tri-pyrrolidinomethane to react to form tetra-pyrrolidino-ethene while tris-(dimethylamino)-methane only dimerizes above 160° C.

When the conventional reaction medium DMF is used, formylation of the cyclic amines takes place in an additional side reaction. When aminomethylenating with DMF acetal in the presence of added cyclic amines, a mixture of the enamines is always obtained, with the cyclic amino compound usually predominating in addition to 10 to 30% of dimethylamino product. This means that about 1 equivalent of the expensive cyclic amine is consumed and, in addition, the same quantity of dimethylamine is liberated and has to be disposed of in an elaborate manner.

Surprisingly, it has been discovered that it is possible to increase the reactivity of dialkylamino-formamide acetals substantially by adding a non-stoichiometric quantity of a non-cyclic secondary amine.

Accordingly, the invention relates to a process for preparing aminomethylene compounds of the formula

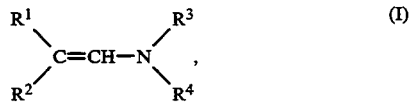

in which $R^1$ represents nitro, cyano, isonitrilo, $COR^9CSR^9$, $COOR^9$, $COSR^9$, $CON(R^9,R^{10})$, $SO_2R^9$, $SO_3R^9$ or $CONH_2$, or an aromatic or heteroaromatic residue which is electron-deficient at the site of preferred nucleophilic attack, $R^2$ can assume the range of meaning of $R^1$, but nevertheless independently of $R^1$, and additionally represents hydrogen, $OR^9$, $SR^9$, $N(R^9,R^{10})$, straight-chain or branched $C_1$–$C_8$-alkyl, $C_2$–$C_8$-alkenyl, $C_2$–$C_8$-alkoxyalkyl, $C_3$–$C_8$-alkoxyalkenyl, $C_3$–$C_8$-cycloalkyl, $C_6$–$C_{12}$-aryl or $C_7$–$C_{10}$-aralkyl, or a 5- to 8-membered, saturated or unsaturated, heterocyclic ring whose 1 or 2 heteroatoms are selected from the group comprising N, O and S, $R^3$ and $R^4$, independently of each other, represent straight-chain or branched $C_1$–$C_8$-alkyl, $C_2$–$C_8$-alkenyl, $C_2$–$C_8$-alkoxyalkyl or $C_3$–$C_8$-alkoxyalkenyl, and $R^9$ and $R^{10}$, independently of each other, represent straight-chain or branched $C_1$–$C_8$-alkyl, $C_2$–$C_8$-alkenyl, $C_2$–$C_8$-alkoxyalkyl, $C_3$–$C_8$-alkoxyalkenyl, $C_3$–$C_8$-cycloalkyl, $C_6$–$C_{12}$-aryl, or $C_7$–$C_{10}$-aralkyl, or a 5- to 8-membered, saturated or unsaturated, heterocyclic ring whose 1 or 2 heteroatoms are selected from the group comprising N, O and S, where, furthermore, $R^9$ and $R^{10}$, together with the N atom which they substitute, can form a 5- to 8-membered ring which can contain a further heteroatom selected from the group comprising N, O and S, which is characterized in that CH-acidic compounds of the formula

are reacted with formamide acetals of the formula

in which $R^1$ to $R^4$ have the said range of meaning and $R^5$ and $R^6$, independently of $R^3$ and $R^4$ and independently of each other, assume the range of meaning stated for $R^3$ and $R^4$, in the presence of a secondary amine of the formula

in which $R^7$ and $R^8$, independently of $R^3$ and $R^4$ and independently of each other, assume the range of meaning stated for $R^3$ and $R^4$, or in the presence of substrates which liberate such amines under the reaction conditions, at 0° to 200° C. with or without solvent, the molar ratio of C—H-acidic compound to formamide acetal being 1:3 to 10:1 and the quantity of secondary amine being 1 to 500 mol %, based on the formamide acetal.

Straight-chain or branched $C_1$–$C_8$-alkyl is, for example, methyl, ethyl, propyl, isopropyl, butyl, isobutyl or tert-butyl, or the isomeric pentyls, hexyls or octyls, preferably the said $C_1$–$C_4$-alkyl radicals.

Straight-chain or branched $C_2$–$C_8$-alkenyl is, for example, vinyl, propenyl or allyl, or the isomeric butenyls, pentenyls, hexenyls or octenyls, preferably the said $C_3$–$C_4$-alkenyl radicals.

Straight-chain or branched $C_2$–$C_8$-alkoxyalkyl is, for example, methoxymethyl, ethoxymethyl and further radicals from the $C_3$–$C_9$-alkyl group in which a $CH_2$ group is replaced by an O atom.

Straight-chain or branched $C_3$–$C_8$-alkoxyalkenyl is, for example, methoxyvinyl, ethoxyvinyl, methoxyallyl, 2-methoxy-propenyl and other radicals from the $C_4$–$C_9$-alkenyl group in which a $CH_2$ group is replaced by an O atom.

$C_3$–$C_8$-Cycloalkyl is, for example, cyclopropyl, methylcyclopropyl, dimethyl-cyclopropyl, cyclobutyl, methylcyclobutyl, cyclopentyl, methyl-cyclopentyl, cyclohexyl, methyl-cyclohexyl, dimethyl-cyclohexyl, cycloheptyl or cyclooctyl, preferably cyclopropyl, cyclopentyl and cyclohexyl, as well as their methyl or dimethyl derivatives.

$C_6$–$C_{12}$-Aryl is, for example, phenyl, naphthyl or biphenyl-yl, preferably phenyl.

$C_7$–$C_{10}$-Aralkyl is, for example, benzyl, 1-phenylethyl or 2-phenylethyl, and further residues of this type which are known to the person skilled in the art, preferably benzyl.

Those carbocyclic or heterocyclic aromatic residues are suitable whose site of linkage to the C atom in formula (II), or to the corresponding site in formula (I), is that which, on account of its relative electron deficiency, is the preferred position for a nucleophilic attack. The person skilled in the art is familiar with this preferred position. The ortho or para positions in nitrobenzene, for instance, represent an important example. Examples of important aromatic residues of this type within the scope of $R^1$ are: 1-imidazolyl, 3-imidazolyl, 2-pyrimidyl, 4-pyrimidyl, 2-nitrophenyl, 4-nitrophenyl, 2,3-dinitrophenyl, 2,4-dinitrophenyl, 2-cyanophenyl, 2,4-dichlorophenyl, 2-pyridyl, 4-pyridyl, 2-quinolyl and 2-carboxyphenyl.

The following may be mentioned as a 5- to 8-membered, saturated or unsaturated, heterocyclic ring whose 1 or 2 heteroatoms are selected from the group comprising N, O and S: pyrrole, furan, thiophene, pyrrolidine, pyrroline, pyrazole, pyrazolidine, imidazole, imidazolidine, thiazole, thiazolidine, oxazole, pyridine, pyrimidine, piperazine, which can be substituted at the N atom by $C_1$–$C_4$-alkyl or by hydroxy-$C_1$–$C_4$-alkyl, morpholine, dioxane, dioxolane, pyran, azepine, azocine, dihydroazocine, isoxazole, dioxolane, dioxazole, isothiazole, pyridazine and pyrazine. It is known to the person skilled in the art that unsaturated heterocyclic rings can have a more or less strongly pronounced aromatic character. The nonaromatic rings morpholine, pyrrolidine and piperidine, which latter can be substituted by $C_1$–$C_4$-alkyl or by hydroxy-$C_1$–$C_4$-alkyl, may be mentioned in a preferred manner.

Formamide acetals can be prepared, for example, by reacting methyleneiminium salts with alcoholates (Chem. Ber. 97, 3397, (1964)).

The reaction of the process according to the invention may be represented by way of example as follows:

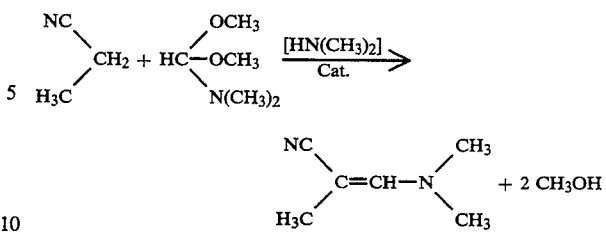

The reaction of the process according to the invention can be carried out without further solvent or diluent if the reagents are liquid. In addition, it can be carried out in the presence of an excess of one of the two reagents if this reagent in excess is liquid. In addition to this, a solvent or diluent can be used.

Solvents which may be employed are those whose acidity is less than that of the C—H-acidic compound and which, under the reaction conditions, either do not enter into exchange or addition reactions with the secondary amine or else do so only to an insignificant extent. Suitable solvents belong to the group comprising alcohols, hydrocarbons, halogenated hydrocarbons, tertiary amines, ketones, amides, in particular dialkylamides, nitriles, ethers, esters, phosphoric acid amides, in particular the peralkyl-phosphoric acid amides, phosphoric acid esters, sulphones, sulpholanes, N-alkyllactams, carbonic acid esters and urea derivatives, in particular peralkyl-urea derivatives. Of the said groups, the solvents which are polar in an aprotic manner and the alcohols are preferred. Examples of solvents from the said groups are:

Petroluem ether, toluene, xylene, chlorotoluene, ligroin, 1,2-dichloroethane, triethylamine, acetone, acetonitrile, tert-butyl acetate, dimethyl carbonate, dimethylacetamide, dimethylformamide (DMF), N-methyl-pyrrolidone (NMP), N-methyl-caprolactam (NMC), tetramethylurea, dimethyl sulphoxide, diethyl sulphone, methyl tert-butyl ether (MTBE), tetrahydrofuran (THF), methanol and isopropanol, preferably acetone, acetonitrile, tert-butyl acetate, dimethyl carbonate, dimethylacetamide, DMF, NMP, NMC, tetramethylurea, dimethyl sulphoxide, diethyl sulphone, MTBE, THF, methanol and isopropanol.

The reaction temperature is from 0° to 200° C., preferably from 20° to 170° C. The reaction time depends on the size of the reaction batch and on the C—H acidity of the starting material as well as on the temperature, and is generally between 0.5 and 36 hours.

The ratio of C—H-acidic compound to formamide acetal is 1:3 to 10:1, preferably 1:2 to 5:1. The proportion of secondary amine does not depend on the stoichiometry of the chemical reaction in the process according to the invention, as formulated by way of example above, and can be 1 to 500 mol %, based on the formamide acetal, preferably 2 to 300 mol % and particularly preferably in the substoichiometric range from 2 to 25 mol %. The substoichiometric quantity, in particular, simplifies conduct of the reaction (low pressure of the reaction system) and disposal of the amine (working up, recycling or incineration). A further advantage of the presence of only a catalytic quantity of secondary amine is the liberal employment of starting materials which enter into an amine exchange, such as can be observed, for example, in the case of esters.

The presence of only a catalytic quantity of secondary amine in amino methylenations using amide acetals is also an advantage as compared with reactions of methyl esters of carboxylic acids with alkoxy-bis-(dialkylamino)-methanes (aminal esters) or tris-(dialkylamino)-methanes, where amide formation can take place to a greater extent as a result of the liberation of 1 or 2 equivalents of amine.

The undesirable formation of amide can be significantly reduced while maintaining the same yield; with regard to this, reference is made to Implementation Example 2.

The precise role of the involvement of secondary amine in the chemical reaction of the process according to the invention is not known with certainty, but is in agreement with the concept that the formamide acetal is present in partially dissociated form. In the presence of the secondary amine, alcohol/amine exchange can take place with the formation of an aminal ester, which possibly represents the actual condensing (aminomethylenating) agent. In this condensation, the secondary amine is eliminated, and is then available once more, so that it only needs to be present in catalytic quantities.

It is known to the person skilled in the art that, in addition to the abovementioned ortho amides, there are also other compounds which can liberate secondary amine under the reaction conditions of the aminomethylenation. These compounds are likewise effective in the said catalytic quantities. Other such compounds are, for example, the salts of weak acids of the secondary amines of the formula (IV), e.g. the carbonates, acetates, propionates etc., and, in addition, the carbamates corresponding to the carbonates, and the $CO_2$ adducts of secondary amines.

EXAMPLES

Example 1

60.7 g of 98% strength DMF-dimethyl acetal, 31 g of acetonitrile and 36.5 g of DMF were reacted together in an 0.3 l V4A autoclave. Dimethylamine was metered in using a sight glass. The yield was determined by means of GC using an internal standard.

| Reaction conditions | Proportion of dimethylamine (in %, based on amount of DMF acetal employed) | Yield (in % of theory) |
| --- | --- | --- |
| 12 h 130° C. | / | 7.2 |
| 234 h 130° C. | / | 15.8 |
| 12 h 130° C. | 25 | 88.7 |
| 12 h 130° C. | 10 | 89.3 |
| 12 h 130° C. | 3.5 | 60.6 |

Example 2

60.7 g of 98% strength DMF acetal, 88 g of ethyl acetate and 36.5 g of DMF were reacted in an analogous manner to Example 1. A mixture of ethyl β-dimethylamino-acrylate and the corresponding methyl ester was obtained. In addition to this, the proportion of dimethylacetamide (DMA) was determined. The quantity of DMA was related to the content of excess ethyl acetate.

| Reaction conditions | Proportion of dimethylamine | Yield (in % of theory) | Dimethylacetamide |
| --- | --- | --- | --- |
| 15 h 140° C. | / | 12.0 | / |
| 10 h 150° C. | 100% | 76.3 | 35% |
| 15 h 140° C. | 50% | 82.0 | 16% |
| 15 h 140° C. | 25% | 83.8 | 5% |
| 15 h 140° C. | 12.5% | 83.1 | 2% |

Example 3

60.7 g of 98% strength DMF acetal, 68.5 g of o-nitrotoluene and 36.5 g of DMF were reacted in an analogous manner.

| Reactiion conditions | Proportion of dimethylamine | Yield (in % of theory) | Observation |
| --- | --- | --- | --- |
| 20 h 120° C. | / | 46.7 | / |
| 20 h 130° C. | / | 54.7 | 10% excess of DMF acetal |
| 20 h 130° C. | 30% | 85.3 | / |
| 20 h 130° C. | 15% | 87.6 | / |
| 20 h 120° C. | 15% | 76.0 | / |

Example 4

132.1 g (1 mol) of dimethylmalonate in 500 ml of methanol were initially introduced into a 1 l four-neck flask, and 9 g (0.2 mol) of dimethylamine were subsequently passed in at room temperature. 119.2 g (1 mol) of DMF-dimethyl acetal were then added within the space of 10 min and the mixture was heated to 50° C. After 1 hour, a sample was removed and analysed using gas chromatography. The extent of conversion to dimethyl dimethylaminomethylene-malonate was 89%. In a comparative experiment without the addition of dimethylamine, a conversion of only 66% was observed after 1 h.

Example 5

Instead of using methanol, the corresponding quantity of DMF was employed in Example 5. After 1 h, the extent of conversion was about 95%.

Example 6

24 g of DMF dimethylacetal, 17.4 g of acetone, 14.6 g of DM and 2.3 g of dimethylamine were heated at 100° C. for 12 hours in a V4A autoclave. After concentrating the mixture under a water-jet vacuum the residue was distilled in a packed column 30 cm in length at 1 mbar. 4-Dimethylamino-3-buten-2-one of 99.6% purity was obtained in a yield of 76.8% of theory.

We claim:

1. Process for preparing aminomethylene compounds of the formula

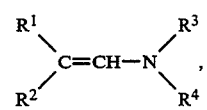

in which $R^1$ represents nitro, cyano, isonitrilo, $COR^9CSR^9$, $COOR^9$, $COSR^9$, $CON(R^9R^{10})$, $SO_2R^9$, $SO_3R^9$, or $CONH_2$, or an aromatic or heteroaromatic residue which is electron-deficient at the site of preferred nucleophilic attack, $R^2$ can assume the range of meaning of $R^1$, independently of $R^1$, and additionally represents hydrogen $OR^9$, $SR^9$, $N(R^9, R^{10})$, straight-chain or branched $C_1$-$C_8$-alkyl, $C_2$-$C_8$-alkenyl, $C_2$-$C_8$-alkoxyalkyl, $C_3$-$C_8$-alkoxyalkenyl, $C_3$-$C_8$-cycloalkyl, $C_6$-$C_{12}$-aryl or $C_7$-$C_{10}$-aralkyl, or a 5- to 8-membered, saturated or unsaturated, heterocyclic ring whose 1 or 2 heteroatoms are selected from the group comprising N, O and S, $R^3$ and $R^4$, independently of each other, represent straight-chain or branched $C_1$-$C_8$-alkyl, $C_2$-$C_8$-alkenyl, $C_2$-$C_8$-alkoxyalkyl or $C_3$-$C_8$-alkoxyalkenyl, and $R^9$ and $R^{10}$, independently of each other, represent straight-chain or branched $C_1$-$C_8$-alkyl, $C_2$-$C_8$-alkenyl, $C_2$-$C_8$-alkoxyalkyl, $C_3$-$C_8$-alkoxyalkenyl, $C_3$-$C_8$-cycloalkyl, $C_6$-$C_{12}$-aryl, or $C_7$-$C_{10}$-aralkyl, or a 5- to 8 -membered, saturated or unsaturated, heterocyclic ring whose 1 or 2 heteroatoms are selected from the group comprising N, O and S, where, furthermore, $R^9$ and $R^{10}$, together with the N atom which they substitute, can form a 5- to 8-membered ring which can contain a further heteroatom selected from the group comprising N, O and S, which is characterized in that CH-acidic compounds of the formula

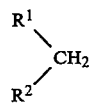

are reacted with formamide acetals of the formula

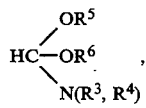

in which $R^1$ to $R^4$ have the said range of meaning and $R^5$ and $R^6$, independently of $R^3$ and $R^4$ and independently of each other, assume the range of meaning stated for $R^3$ and $R^4$, in the presence of a secondary amine of the formula

in which $R^7$ and $R^8$, independently of $R^3$ and $R^4$ and independently of each other, assume the range of meaning of $R^3$ and $R^4$, or in the presence of substrates which liberate such amines under the reaction conditions, at 0° to 200° C. with or without solvent, the molar ratio of C—H-acidic compound to formamide acetal being 1:3 to 10:1 and the quantity of secondary amine being 1 to 500 mol %, based on the formamide acetal.

2. Process according to claim 1, characterized in that the reaction is carried out at 20° to 170° C.

3. Process according to claim 1, characterized in that the molar ratio of C—H-acidic compound to formamide acetal is 1:2 to 5:1.

4. Process according to claim 1, characterized in that the quantity of secondary amine is 2 to 300 mol %, based on formamide acetal.

5. Process according to claim 4, characterized in that the quantity of secondary amine is 2 to 25 mol %, based on formamide acetal.

6. Process according to claim 1, characterized in that, when a solvent is used, either one selected from the group comprising alcohols, hydrocarbons, halogenated hydrocarbons, tertiary amines, ketones, amides, nitriles, ethers, esters, phosphoric acid amides and phosphoric acid esters, sulphones, sulpholanes, N-alkyllactams, carbonates and urea derivatives, or else a mixture of a number of these, is employed.

7. Process according to claim 6, characterized in that a solvent is employed which is selected from the group comprising the alcohols, ketones, nitriles, esters, carbonates, carboxamides, N-alkyllactams, tetraalkylureas, dialkyl sulphoxides, dialkyl sulphones and ethers.

* * * * *

UNITED STATES PATENT AND TRADEMARK OFFICE
CERTIFICATE OF CORRECTION

PATENT NO. : 5,401,869

DATED : March 28, 1995

INVENTOR(S) : Kraus, et al.

It is certified that error appears in the above-identified patent and that said Letters Patent is hereby corrected as shown below:

Col. 1, line 67  After " $COR^9$ " insert -- , --

Col. 6, line 66  After " $COR^9$ " insert -- , --

Signed and Sealed this

Sixth Day of June, 1995

Attest:

BRUCE LEHMAN

*Attesting Officer*  *Commissioner of Patents and Trademarks*